(12) United States Patent
Hazrati et al.

(10) Patent No.: US 8,764,272 B2
(45) Date of Patent: Jul. 1, 2014

(54) METHOD FOR MONITORING THIXOTROPY IN CONCRETE MIXING DRUM

(75) Inventors: Kati Hazrati, Boston, MA (US); Ara A. Jeknavorian, Chelmsford, MA (US); Eric Koehler, Woburn, MA (US)

(73) Assignee: W. R. Grace & Co., -Conn., Columbia, MD (US)

( * ) Notice: Subject to any disclaimer, the term of this patent is extended or adjusted under 35 U.S.C. 154(b) by 890 days.

(21) Appl. No.: 12/933,947

(22) PCT Filed: Apr. 7, 2008

(86) PCT No.: PCT/US2008/059552
§ 371 (c)(1), (2), (4) Date: Sep. 22, 2010

(87) PCT Pub. No.: WO2009/126138
PCT Pub. Date: Oct. 15, 2009

(65) Prior Publication Data
US 2011/0029134 A1 Feb. 3, 2011

(51) Int. Cl.
| | |
|---|---|
| *G05B 21/00* | (2006.01) |
| *B28C 7/02* | (2006.01) |
| *G01N 33/38* | (2006.01) |
| *C04B 40/00* | (2006.01) |
| *C04B 111/00* | (2006.01) |
| *G01N 11/00* | (2006.01) |

(52) U.S. Cl.
CPC .............. *B28C 7/026* (2013.01); *G01N 33/383* (2013.01); *C04B 40/0028* (2013.01); *C04B 2111/0012* (2013.01); *G01N 2011/0046* (2013.01)
USPC ...... 366/2; 366/6; 366/17; 366/142; 73/54.31; 700/265

(58) Field of Classification Search
CPC .................. C01B 40/0028; B04B 2111/0012; G01N 33/383
USPC .................. 366/1, 2, 6, 142; 73/54.32, 54.31; 700/265
See application file for complete search history.

(56) References Cited

U.S. PATENT DOCUMENTS

| | | |
|---|---|---|
| 1,730,893 A | 10/1929 | Lichtenberg |
| 1,898,890 A | 2/1933 | Perry |

(Continued)

FOREIGN PATENT DOCUMENTS

| | | |
|---|---|---|
| EP | 0126573 | 11/1984 |
| EP | 1693352 | 8/2006 |

(Continued)

OTHER PUBLICATIONS

Tattersall, "The Rheology of Fresh Concrete", Pitman, (1983), 106 pages.

(Continued)

*Primary Examiner* — Tony G Soohoo
(74) *Attorney, Agent, or Firm* — Craig K. Loen

(57) ABSTRACT

The invention provides 'thixotropy' monitoring, by measuring the reversible, time-dependent reduction in viscosity occurring when concrete is subjected to mixing, and employs a mixing drum and conventional slump monitoring equipment as used on ready-mix trucks. In one embodiment, the drum is rotated until concrete is completely mixed; the speed is altered, such as by increasing it to a predetermined level; and the energy required to rotate the drum (ER) is monitored; the maximum (ER-MAX) and minimum (ER-MIN) values are recorded in computer memory; and these values are compared to pre-determined (target) values. Rheology factors (including viscosity, yield stress, and/or thixotropy) can be adjusted accordingly by adding liquid component(s) into the mix. This method, suitable for delivery of highly fluid concrete speed such as SCC, can involve transit and placement rheology targets during monitoring.

15 Claims, 9 Drawing Sheets

(56) References Cited

U.S. PATENT DOCUMENTS

| | | | |
|---|---|---|---|
| 1,980,184 A | 11/1934 | Butcher | |
| 2,013,837 A | 9/1935 | Perry | |
| 2,089,604 A | 8/1937 | Hagy | |
| 2,339,991 A | 1/1944 | Hagy | |
| 2,342,749 A | 2/1944 | Maxon, Jr. | |
| 2,409,014 A | 10/1946 | Bohmer et al. | |
| 2,558,248 A | 6/1951 | Heidegger | |
| 2,629,790 A | 2/1953 | Laing et al. | |
| 2,643,542 A | 6/1953 | Cronk et al. | |
| 2,821,079 A | 1/1958 | Kerridge | |
| 3,237,437 A | 3/1966 | Hilkemeier | |
| 3,403,546 A | 10/1968 | Stratton | |
| 3,582,969 A * | 6/1971 | Kinney | 377/15 |
| 3,631,712 A | 1/1972 | Mercier | |
| 3,640,121 A | 2/1972 | Mercier | |
| 3,731,909 A | 5/1973 | Johnson | |
| 3,803,903 A * | 4/1974 | Lin | 73/54.31 |
| 3,924,447 A | 12/1975 | Garrison | |
| 4,008,093 A | 2/1977 | Kitsuda et al. | |
| 4,027,859 A * | 6/1977 | Stone | 366/142 |
| 4,318,177 A | 3/1982 | Rapp | |
| 4,332,158 A | 6/1982 | Osborne | |
| 4,356,723 A | 11/1982 | Fay | |
| 4,522,499 A | 6/1985 | Hudelmaier | |
| 4,544,275 A | 10/1985 | Hudelmaier | |
| 4,900,154 A | 2/1990 | Waitzinger | |
| 5,456,105 A * | 10/1995 | James | 73/54.31 |
| 5,541,855 A | 7/1996 | Enzler | |
| 5,713,663 A | 2/1998 | Zandberg | |
| 5,752,768 A | 5/1998 | Assh | |
| 5,948,970 A | 9/1999 | Te'eni | |
| 6,042,258 A | 3/2000 | Hines | |
| 6,042,259 A | 3/2000 | Hines | |
| 6,227,039 B1 | 5/2001 | Te'eni | |
| 6,286,987 B1 * | 9/2001 | Goode et al. | 366/60 |
| 6,484,079 B2 | 11/2002 | Buckelew et al. | |
| 6,874,353 B2 * | 4/2005 | Johnson et al. | 73/54.31 |
| 6,997,045 B2 | 2/2006 | Wallevik | |
| 7,021,123 B2 | 4/2006 | Wallevik | |
| 7,384,180 B2 | 6/2008 | Jarvinen et al. | |
| 7,624,625 B2 * | 12/2009 | Jau | 73/54.31 |
| 8,491,717 B2 * | 7/2013 | Koehler et al. | 366/8 |
| 2003/0172850 A1 | 9/2003 | Chun et al. | |
| 2004/0072715 A1 | 4/2004 | Griese et al. | |
| 2004/0149019 A1 * | 8/2004 | Johnson et al. | 73/54.31 |
| 2004/0198873 A1 | 10/2004 | Bury et al. | |
| 2005/0141338 A1 | 6/2005 | Jarvinen | |
| 2005/0252420 A1 | 11/2005 | Timmons | |
| 2006/0287773 A1 | 12/2006 | Anderson et al. | |
| 2007/0185636 A1 | 8/2007 | Cooley et al. | |
| 2008/0009976 A1 | 1/2008 | Anderson et al. | |
| 2008/0027583 A1 | 1/2008 | Anderson et al. | |
| 2008/0027584 A1 | 1/2008 | Anderson et al. | |
| 2008/0027685 A1 | 1/2008 | Anderson et al. | |
| 2008/0060423 A1 * | 3/2008 | Jau | 73/54.31 |
| 2011/0029134 A1 * | 2/2011 | Hazrati et al. | 700/265 |

FOREIGN PATENT DOCUMENTS

| | | |
|---|---|---|
| GB | 1182590 | 3/1970 |
| GB | 2329502 | 3/2004 |
| GB | 2426347 | 2/2007 |
| WO | 9858887 | 12/1998 |
| WO | 2005080058 | 9/2005 |
| WO | 2006032785 | 3/2006 |

OTHER PUBLICATIONS

Amziane, "Measurement of Workability of Fresh Concrete Using a Mixing Truck", J. Res. Natl. Inst Stand. Technol. 110, 55-66 (2005).

Daczko, "A Proposal for Measuring Rheology of Production Concrete,". Concrete International, 22 (5),47-49, (2000).

Ready Slump Brochure, On-board Ready Mix Process Control, RS Solutions LLC, (2004), 7 pages.

Koehler, "Aggregates in self consolidating concrete", The University of Texas at Austin, (2007), 362 pages.

Koehler, "Static and Dynamic Yield Stress Measurements of SCC", SCC 2008 Conference Proceedings, 6 pages.

Young, Form PCT/ISA/210, International Search Report, PCT/US2008/059552, 2pp., 2008.

Young, Form PCT/ISA/237, Written Opinion of the International Searching Authority, PCT/US2008/059552, 6pp,, 2008.

Soohoo, Form PCT/IPEA/409, International Preliminary Report on Patentability, PCT/US2008/059552, 11pp., 2010.

* cited by examiner

Y = first rheological parameter
V = second rheological parameter $t_0$ = batching time
$t_1$ = current time
$t_2$ = delayed addition
$t_3$ = placement time A = no additive, improper rheology
B = additive #1, incorrect combination of Y and V
C = additive #2, correct rheology at placement
D = additive #3, correct rheology at placement

METHOD FOR MONITORING THIXOTROPY IN CONCRETE MIXING DRUM

FIELD OF THE INVENTION

The present invention relates to manufacturing of concrete, and more particularly to a method for monitoring and control of thixotropy of concrete in a mixing drum.

BACKGROUND OF THE INVENTION

The monitoring and control of concrete "slump" in ready-mix delivery trucks has been described in a number of published patent documents, which are summarized below and incorporated herein by reference.

In U.S. Pat. No. 4,008,093, Kitsuda et al. disclosed that the slump property of a concrete mix could be controlled by measuring electrical energy required for rotating the mixing drum and allowing the truck operator to adjust slump by adding water to maintain it within a certain slump range, thereby making longer transportation of concrete by truck mixer possible.

In U.S. Pat. No. 5,713,663, Zandberg disclosed that concrete slump could be controlled by monitoring torque on the hydraulic drive of the truck mixing drum and automatically adding a liquid component to adjust the concrete mix to a desired slump, as detected by a minimum torque loading on the mixing drum.

In U.S. Pat. No. 6,484,079, Buckelew et al. disclosed that the slump control of Zandberg et al. could be remotely monitored. The status of the delivery truck could be reported and tracked using wireless transmission and global positioning units.

In application Ser. No. 09/845,660 (Publication No. US2002/0015354A1), Buckelew disclosed that continuous monitoring of slump, using GPS positioning systems, could help to detect whether the truck operator or construction foreman added water to make the concrete easier to spread (paragraphs 0005-0006). This unauthorized addition of water could work detriment to the concrete mix by decreasing compressive strength. Thus, Buckelew taught that slump be monitored numerous times during delivery, and the slump data downloaded by wireless transfer at the installation site.

In U.S. application Ser. No. 10/599,130 (Publication No. 2007/01856A1), Cooley et al. disclosed a system for calculating and reporting slump in a truck drum that had a hydraulic sensor coupled to the hydraulic drive and a rotational speed sensor connected to the drum. Both sensors were connected to a wireless communication system. This permitted modifications to be made to the truck operation during the delivery service.

The monitoring of concrete slump involves calibrating the values obtained from the hydraulic or electrical sensor on a mixing truck and correlating these with slump values obtained using a standard slump cone test. In a standard slump cone test, a 12-inch truncated cone containing fresh concrete is removed to permit the concrete to drop, and the vertical height drop of the concrete is measured (ASTM C143-05).

The present inventors believe that the slump of a concrete mix does not provide an accurate indication of its segregation resistance. This resistance to segregation refers to the ability of the concrete mix to cohere with uniform consistency such that separation of component solids is avoided. Concrete is a suspension made from mixing water, cement, and aggregate (e.g., sand, crushed gravel). The denser material (usually aggregate) tends to sink downwards when mixing stops. The turn-screw effect of the blades or paddles mounted inside the rotating drum of the truck can exacerbate segregation by pushing the aggregate in one direction along the axis of drum rotation.

Segregation can lead to diminishment of the concrete mix "pumpability" (i.e., ability to be conveyed through a conduit) as well as of its "finishability" (i.e., ability to provide smooth but dense outer surface). On the other hand, it is important to control cohesiveness so that it does not become excessive to the point of hindering ease of pumping or finishability.

In U.S. Pat. No. 6,227,039, Te'eni stated that "different concrete mixes can exhibit equal workabilities (slump) when measured by different techniques and yet can possess totally different rheological properties relating to their suitability for commonly required applications," such as pumping (col. 2, II. 14-20). He disclosed a shearing sensor unit having vibrating and shear-inducing devices and sensors for measuring stress and acceleration (FIG. 1; col. 6-7). A piston pushed the shear box downwards, forcing the concrete sideways out of open ends of a U-shaped shear box, where multiple sensors monitored the resistance to movement of the piston rod (col. 7, I. 59—col. 8, I. 9). The shear box could be mounted within the truck drum to transmit data wirelessly to a mixing plant so that a rheological profile could be generated based on workability, stress state sensitivity, stress distribution, shear rate sensitivity, vibration decay, vibratability, pumpability, and deformability (col. 8, II. 59—col. 9, II. 39).

However, mounting the U-shaped box shear-sensing device of Te'eni within the mixing drum of a concrete delivery truck would appear problematic. The truck operator would need to ensure that the shear box was submerged under the concrete mix, rather than located upside down within the drum above the concrete mix, so that the sensors could operate properly. The truck operator might be required to shut down the engine to ensure that its vibration would not interfere with the operation of the vibration sensors on the shear box. Moreover, during transit, the shear box would likely be crushed by the tremendous weight of the aggregate, leading to repair problems. Having a shear box protruding within the mixing drum could also interfere with operation of the mixing paddles on the concrete mix.

Thus, an objective of the present invention is to monitor and to control the rheology of the concrete mix during transit from the ready-mix plant (or dispatch center) to the site of placement (or pouring), using the truck's mixing drum as a rheometer and monitoring equipment that is presently available in the concrete industry, without having to mount U-boxes or other pneumatic or vibratory devices within the drum.

Another objective of the present invention is to minimize the number of rheology factors that require assessment and to avoid having to analyze certain factors, such as vibration decay or vibratability, altogether.

A further objective of the present invention is to provide a method for controlling the rheology of highly flowable concretes, such as Self Consolidating Concrete ("SCC"). SCC is concrete that is able to flow and to consolidate under its own mass without vibration. SCC is highly filled, with typically about 70% aggregate by volume, as well as highly fluid. Due to this high degree of fluidity (characterized as "slump flow"), the horizontal flow (spread) rather than the vertical drop of the concrete placed in a slump cone is measured (ASTM C 1611-05). SCC typically exhibits 18-32 inch slump flow when measured by this slump cone method.

The prior art for estimating slump in a concrete mixer does not provide for estimation or monitoring of slump flow. Moreover, the use of the afore-mentioned slump cone method for measuring slump flow is not believed by the present inventors to provide an accurate means for assessing SCC or other highly fluid concrete mixes.

Hence, a novel method for monitoring and control of rheology of concrete mixes in a concrete delivery mixing truck is needed.

SUMMARY OF THE INVENTION

In surmounting the disadvantages of the prior art, the present invention provides a novel method for monitoring and control of thixotropy in concrete mixing drums, including those installed on delivery mix trucks, thus allowing monitoring and control of thixotropy while in transit from plant to placement. The method can be used with conventional slump monitoring equipment on such delivery trucks, and is preferably used to supplement conventional slump monitoring.

The novel method of the present invention builds inventively upon the approach of Amziane, Ferraris and Koehler in "Measurement of Workability of Fresh Concrete Using a Mixing Truck," *Journal of Research of the National Institute of Standards and Technology* (Vol. 110, No. 1, January-February 2005, pages 55-66), which is incorporated herein by reference. Amziane et al. taught that yield stress and plastic viscosity were important for studying flow behavior; and furthermore that the power (required to rotate the drum) and shear rate (rotation speed) could be plotted on a graph, so that slope of the resulting curve indicated plastic viscosity, while the intercept of the curve at zero shear rate indicated the yield stress.

The present invention employs conventional slump monitoring systems to monitor a rheology factor known as "thixotropy." While "yield stress" refers to the amount of mixing force required for initiating flow and "plastic viscosity" refers to the resistance to flow once yield stress is exceeded, the term "thixotropy" refers to the reversible, time-dependent reduction in viscosity that occurs when the concrete is subjected to shear forces (e.g., mixing). When concrete is at rest, a thixotropic internal structure is formed by internal bonding of the hydrating cement and other forces. The result is a high static yield stress reflected by the amount of energy required to start mixing the material. Mixing forces work to disrupt the thixotropic structure, lowering the resistance to flow, but the thixotropic internal structure returns when shearing (mixing) forces diminish.

An exemplary method of the present invention for monitoring thixotropy of a concrete mix comprises: (A) rotating a concrete mix, or the components of a concrete mix, in a concrete mixing drum at a first mixing speed ($S_1$) to mix completely the concrete mix components or otherwise to maintain the concrete mix in a completely mixed state; and (B) measuring the thixotropy of the concrete mix by monitoring the reversible, time dependent change in viscosity occurring after rotational speed of the concrete mix in the mixing drum is altered by changing to another speed ($S_2$) that is different from $S_1$ (e.g., preferably $S_2$ is greater than $S_1$).

An example of the method of the invention involves measuring energy after speed increase. This exemplary method comprises, after step A, increasing the speed of the mixing drum to a faster constant mixing speed $S_2$ such that $S_2$ is at least one half revolution per minute faster than $S_1$; monitoring the energy required to rotate the mixing drum ($E_R$) at constant speed $S_2$ until after $E_R$ levels off over time; storing in computer (accessible) memory a first value corresponding to the maximum energy required to rotate the mixing drum ($E_{R\text{-}MAX}$) after increasing the mixing speed from $S_1$ to $S_2$ and also storing in computer memory a second value corresponding to the average energy required to rotate the mixing drum during a predetermined time period wherein the energy required to rotate continuously the mixing drum at constant speed $S_2$ begins to level off to a minimum level ($E_{R\text{-}MIN}$) after dropping from $E_{R\text{-}MAX}$; comparing said $E_{R\text{-}MAX}$ and $E_{R\text{-}MIN}$ values to at least one set of predetermined target values stored in computer memory; and adjusting yield stress, plastic viscosity, or thixotropy of said concrete mix contained in said rotating mixing drum using a liquid component.

One can therefore measure the overall decrease in energy required to rotate the mixing drum after increasing drum speed. (The inventors refer to this as the "torque fade" variation of the method of the invention). Accordingly, one can derive a value by taking the difference between (or the ratio of) $E_{R\text{-}MAX}$ and $E_{R\text{-}MIN}$ and by comparing this value to predetermined (target) rheology value ranges stored in computer memory (e.g., ranges based on differences between, or ratios of, predetermined $E_{R\text{-}MAX}$ and $E_{R\text{-}MIN}$ values).

Another preferred example involves measuring energy required to rotate the mixing drum in each of the periods after increasing and after decreasing drum speed. The inventors call this the "trapezoid" variation, because plotting the resultant $E_R$ values against speed on a graph produces a trapezoid shape. This variation of the method comprises, after step A, rotating the mixing drum at a higher speed (than mixing speed $S_1$ in step A), or more preferably at constant speeds that are increased in step-wise fashion, for specified time periods. The energy needed for rotating the concrete mix ($E_R$) at each speed interval is determined. These $E_R$ values are stored in computer memory. (If depicted on a two-dimensional graph, these $E_R$ values would illustrate a first stress curve in terms of $E_R$ vs. speed). The concrete mix is rotated at the same higher speed and $E_R$ is again calculated for the specified time period, but only once $E_R$ has leveled off. Again, this leveling-off illustrates an aspect of the thixotropy of the concrete mix. In other words, mixing causes a breakdown of the three-dimensional structure formed due to thixotropy, which results in lower resistance flow for a given shear rate (mixing speed). When a constant, minimum resistance to flow is achieved for a given mixing speed, the thixotropic built-up structure is disrupted. Upon a reduction in shear rate (mixing speed), the thixotropy built-up structure is restored. This procedure (wherein $E_R$ is again calculated for the specified time period but only once $E_R$ has leveled off) is repeated at a different speed (this time at preferably a lower speed rather than at higher speed) so that a second set of $E_R$ values can be determined and stored in computer memory (and more preferably a succession of progressively lower speeds is used and measured at such lower speeds for the specified time). (If depicted on a two-dimensional graph, this second set of $E_R$ values would illustrate a second stress curve in terms of $E_R$ vs. speed). A thixotropy value (corresponding to trapezoid area between stress curves when plotted on a graph) is compared to predetermined (target) ranges stored in computer-accessible memory.

Thus, another exemplary method of the invention for monitoring concrete rheology comprises: rotating a concrete mix, or the components of a concrete mix, in a concrete mixing drum at a first mixing speed ($S_1$) to mix completely the concrete mix components or otherwise to maintain the concrete mix in a completely mixed state; rotating said concrete mix at a first constant drum speed ($S_1$) and at least one higher speed ($S_2$) for specified time periods to determine the energy needed for rotating the concrete mix ($E_R$) at each speed; storing said determined first energy value ($E_{R1}$) and second energy ($E_{R2}$) values in computer memory; rotating said concrete mix at $S_2$ to determine a third energy value ($E_{R3}$) for a specified time period, but determining the third energy value ($E_{R3}$) only after $E_R$ has leveled off (thereby indicating the thixotropy of the concrete mix), and storing $E_{R3}$ in computer memory; rotating said concrete mix at a speed ($S_3$) different from (and this time preferably lower than) $S_2$ to determine a fourth energy value ($E_{R4}$) for a specified time period, but determining a fourth energy value ($E_{R4}$) only after $E_R$ has leveled off (thereby indicating that the concrete mix has reached a minimum resistance to flow for the given mixing speed), and storing $E_{R4}$ in computer memory; comparing relative rheology values (in terms of at least two values selected from yield stress, plastic viscosity, and thixotropy) based on said determined $E_{R1}$, $E_{R2}$, $E_{R3}$, and $E_{R4}$ values with predetermined values (in terms of at least two values selected from yield stress, plastic viscosity, and thixotropy) stored in computer memory; and adjusting rheology of said concrete mix using a liquid component.

The methods of the present invention are suitable for controlling concrete rheology on delivery vehicles (e.g., trucks) having a mixing drum and automated slump monitoring and liquid dispensing equipment. Thixotropy as well as slump and other rheology values can be adjusted automatically and kept with predetermined (target) ranges. The invention is suitable for highly fluid concrete such as self-consolidating concrete (SCC). Ideally, SCC should possess a low yield stress so that it flows and consolidates under its own mass; but its static yield stress, when mixing forces diminish, should allow it to resist segregation and partially to support its own weight, reducing lateral forces transmitted to formwork (mold). At placement, it is desirable for SCC to have a slump flow of 18-32 inches; but during transit, this high fluidity could give rise to splashing on bumpy or elevated roads, causing material loss (through mixing drum opening) and lack of accuracy in slump monitoring.

It is therefore useful to lower slump during transport to between 0-11 inches (cone test) and to employ the thixotropy monitoring method of the present invention. At some point during delivery, the decision is made to increase slump and to monitor thixotropy to confirm that it meets a "placement profile" (e.g., for SCC). Exemplary methods thus comprise converting the mode of the truck monitoring system from a predetermined (target) transit rheology to a placement rheology. The point of conversion can be determined by considering temperature (ambient and concrete), humidity, concrete mixture proportions, time to discharge, time required for converting from transit to placement rheology, nature of the terrain (e.g., whether smooth, bumpy, elevated), and other inputs (e.g., estimated time of arrival using GPS).

For SCC applications in particular, it is desirable to ensure that the rheology factors (yield stress, plastic viscosity, and thixotropy) are monitored, because avoiding segregation during transit is important for avoiding segregation when SCC is placed (discharged) into the formwork.

Further advantages and features of the invention may be described hereinafter.

BRIEF DESCRIPTION OF THE DRAWINGS

Further advantages and features of the present invention may be more readily comprehended when the following detailed description of preferred embodiments is taken in conjunction with the appended drawings wherein.

DETAILED DESCRIPTION OF EXEMPLARY EMBODIMENTS

The present inventors contemplate that methods of the invention for controlling rheology of concrete mixes during the delivery operation from the batching plant or central dispatch center and to the placement site (e.g., the construction site where the mix is discharged from the truck) can be performed using known slump control systems that are commercially available for concrete delivery trucks. Such concrete mixes conventionally contain a hydratable cementitious binder (such as ordinary portland cement, fly ash, granulated blast furnace slag, gypsum, or mixture or mixtures thereof), an aggregate portion (sand, crushed stone or gravel, and usually both), water (for hydrating the binder), and one or more chemical admixtures (such as water-reducing agents or high range water-reducing agents, viscosity modifying agents, corrosion-inhibitors, and the like). Concrete delivery mixing trucks having slump control monitoring and control equipment, such as hydraulic or electric sensors for measuring the energy for rotating the mixing drum, speed sensors for measuring the speed of rotation, temperature sensors for monitoring the atmospheric temperature as well as the mix temperature, and dispensing equipment, as well as the computer processing units for monitoring signals from the sensors and actuating the dispensing equipment are by now relatively well known in the industry.

For example, such slump control systems, which can be used in association with wireless communication systems, are disclosed in U.S. Pat. Nos. 5,713,663 and 6,484,079, and in U.S. Ser. No. 09/845,660 (publication no. 2002/0015354A1) and U.S. Ser. No. 10/599,130 (publication no. 2007/01856A1), as previously discussed in the background and incorporated herein by reference. Another exemplary system for monitoring and control using wireless communications in combination with sensors for monitoring various physical properties of the concrete mix is also taught in U.S. Pat. No. 6,611,755 of Coffee, which is incorporated herein by reference.

Hardware and software for monitoring and control of slump on concrete delivery trucks is commercially available from RS Solutions under the READYSLUMP® trade name.

It should also be noted here that many, if not most, commercially available slump control systems require that the driver manually adjust the speed of the drum. However, the present inventors believe that it is preferable to employ closed loop speed control systems. In other words, the rotational speed of the drum is preferably automatically selected, monitored, and controlled by computer, so as to minimize human error and involvement (and also to allow the driver to pay attention to driving). Hence, exemplary methods of the invention comprise the use of closed loop speed control systems to control the rotational speed of the concrete mixing drum.

Figure 1:
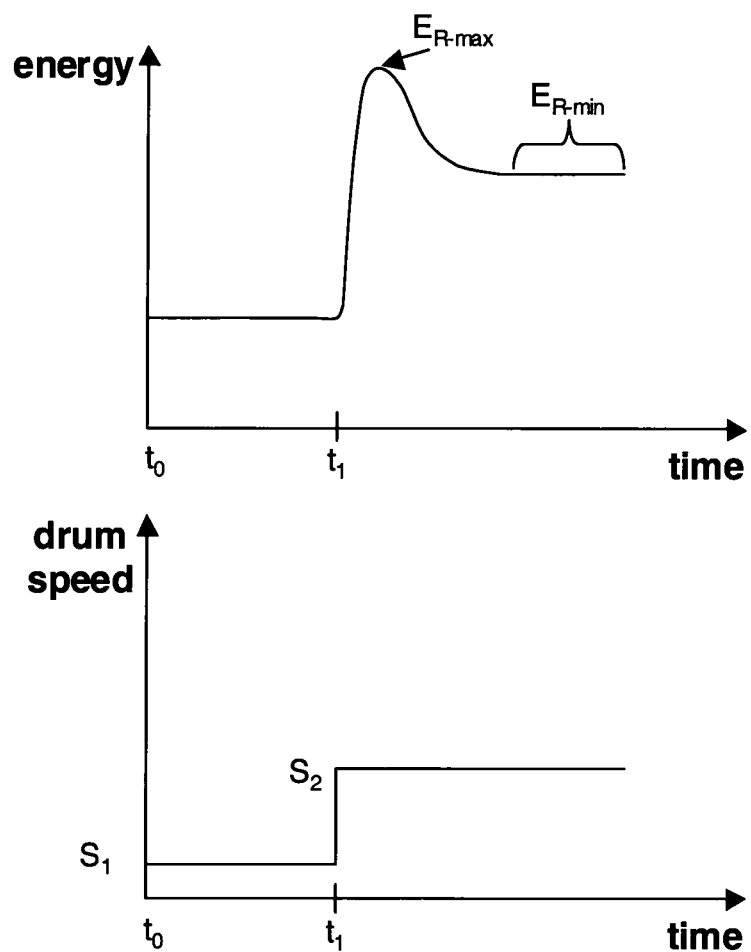
FIG. 1 is a composite graphical illustration

The juxtaposed graphs in FIG. 1 illustrate an exemplary method of the present invention (what the inventors previously referred to as the "torque fade" variation) for monitoring thixotropy of a concrete mix in terms of measuring the energy required to turn the concrete mix ($E_R$) over time (upper graph) as well as the drum speed (S) over time (lower graph). The graphs are juxtaposed so that energy and drum speed increase can be viewed simultaneously against time.

The exemplary method begins by rotating a concrete mix, or the components of a concrete mix, in a concrete mixing drum at a first mixing speed ($S_1$) to mix completely the concrete mix components or otherwise to maintain the concrete mix in a completely mixed state, as evidenced by little or no fluctuation of $E_R$ between $t_0$ and $t_1$ (upper graph). As previously discussed, the components of the concrete mix include liquid components (e.g., water, chemical admixtures such as high range water reducers (HRWR), and viscosity modifying agents (VMA)), which are added at the mixing plant into the mixing truck and can be added by the automatic liquid dispensing equipment on a concrete delivery truck during the delivery operation. The objective of mixing is to ensure that the concrete components are mixed completely; or, in other words, the mix and/or components are introduced into the mixing drum, which is rotated until a uniform paste consistency is obtained. While this can be done empirically, confirmation of complete mixing is preferably done by rotating the mixing drum at constant speed while measuring the energy required for rotating the drum ($E_R$) until a predetermined minimum fluctuation of $E_R$ over time is obtained.

As shown in the lower graph of FIG. 1, the speed of the drum between $t_0$ and $t_1$ is $S_1$, which is increased to $S_2$ at $t_1$. As shown in the upper graph, thixotropy is monitored by measuring the reversible, time dependent change in viscosity occurring after $t_1$. $E_R$ is seen to increase (corresponding to the amount of thixotropic internal structure in the concrete mix corresponding to $S_2$) until $E_R$ reaches a maximum ($E_{R-MAX}$), and thereafter $E_R$ begins to drop and eventually to "level off" ($E_{R-MIN}$). This $E_R$ value is stored in computer (-accessible) memory, and corresponds to the maximum energy required to rotate the mixing drum ($E_{R-MAX}$) after increasing the mixing speed from $S_1$ to $S_2$. The system continues to monitor $E_R$ and stores in computer memory a second value corresponding to the average energy required to rotate the mixing drum during a predetermined time period wherein the energy required to rotate continuously the mixing drum at constant speed $S_2$ begins to level off to a minimum level ($E_{R-MIN}$).

The derived $E_{R-MAX}$ and $E_{R-MIN}$ values are then compared to at least one set of predetermined (target) values stored in computer memory. This can be done by taking the difference between $E_{R-MAX}$ and $E_{R-MIN}$, and comparing the difference value to a range of predetermined difference values (e.g., $E_{R-MAX}$ minus $E_{R-MIN}$) stored in computer memory; or by taking the ratio of $E_{R-MAX}$ and $E_{R-MIN}$ and comparing this ratio value to a range of predetermined ratio values (e.g., $E_{R-MAX}/E_{R-MIN}$) stored in computer memory.

If the derived value for the difference between, or ratio of, $E_{R-MAX}$ and $E_{R-MIN}$ do not fall within the range of predetermined (target) values, then the invention further involves adjusting rheology by using a liquid component (e.g., water, high range water reducer, viscosity modifying agent) in order to bring the rheology of the concrete within the predetermined (target) rheology range.

It was previously mentioned that measuring thixotropy is usually faster after increasing speed because less time is required for breaking down thixotropic internal structure than for building it back up to the level corresponding to the particular mixing speed. When measuring thixotropy after increasing speed ("torque fade" variation), one may, for example, increase speed by half revolution of the mixing drum per minute (rpm). However, for increased accuracy, it may be advisable to increase speed by at least 1 and more preferably 2 rpm or more. When measuring thixotropy after decreasing speed, it is preferable to decrease the rotational speed by at least 2 and more preferably 3 rpm to increase accuracy of detecting and calculating $E_{R-MIN}$ values corresponding to the particular speed at which the mixing drum is rotated.

Thus, an exemplary method of the invention for measuring energy after increases in speed reveals the "torque fade" characteristic of this kind of thixotropy monitoring. This exemplary method comprises, rotating a concrete mix, or the components of a concrete mix, in a concrete mixing drum at a first mixing speed ($S_1$) to mix completely the concrete mix components or otherwise to maintain the concrete mix in a completely mixed state); then increasing the speed of the mixing drum to a faster constant mixing speed $S_2$ such that $S_2$ is at least one half revolution per minute (rpm) and more preferably at least one rpm faster than $S_1$; monitoring the energy required to rotate the mixing drum ($E_R$) at constant speed $S_2$ until after $E_R$ levels off over time; storing in computer memory a first value corresponding to the maximum energy required to rotate the mixing drum ($E_{R-MAX}$) after increasing the mixing speed from $S_1$ to $S_2$ and also storing in computer memory a second value corresponding to the average energy required to rotate the mixing drum during a predetermined time period wherein the energy required to rotate continuously the mixing drum at constant speed $S_2$ begins to level off to a minimum level ($E_{R-MIN}$) after dropping from $E_{R-MAX}$; comparing said $E_{R-MAX}$ and $E_{R-MIN}$ values to at least one set of predetermined target values stored in computer memory; and adjusting yield stress, plastic viscosity, and/or thixotropy of said concrete mix contained in said rotating mixing drum using a liquid component (e.g., water, high range water reducer, viscosity modifying agent).

Another exemplary method of the invention for monitoring and controlling thixotropy of concrete mixes involves both increasing and decreasing the rotational speeds of the mixing drum.

Figure 2:
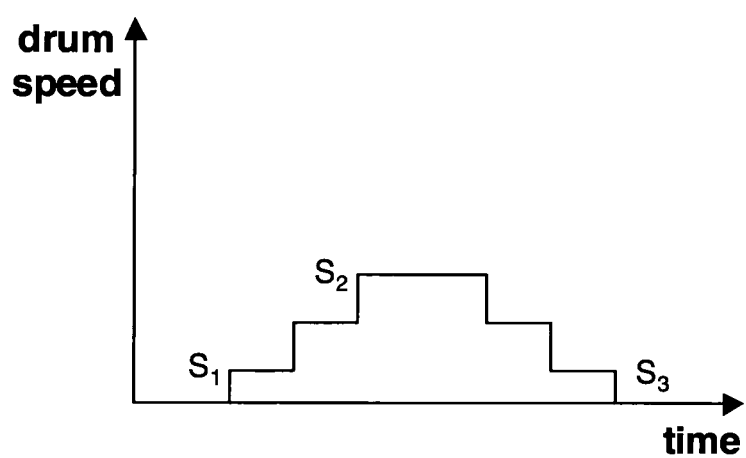
FIG. 2 is a graphical illustration of an aspect of an exemplary method of the invention wherein the rotational speed of a mixing drum containing a fresh concrete mix is increased by increments over periods of time.
Figure 3A:
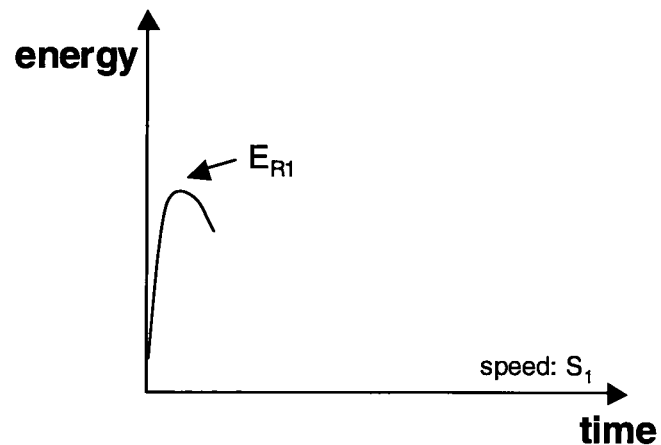
FIG. 3A is a graphical illustration of an exemplary method of the invention wherein the energy required to rotate the mixing drum containing a fresh concrete mix is continuously measured at a first constant rotation speed ($S_1$) for a continuous period of time.
Figure 3B:
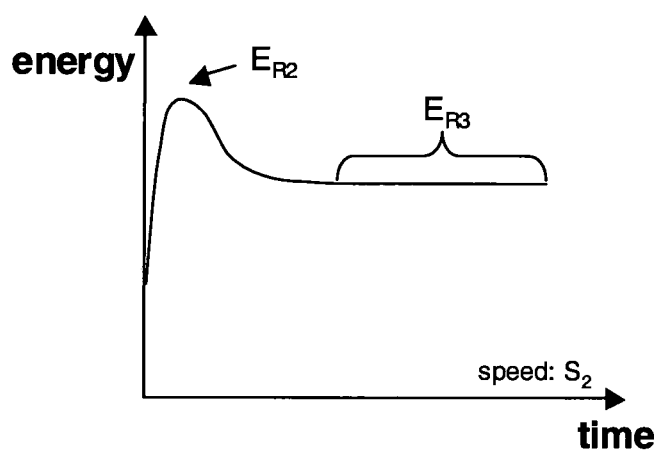
FIG. 3B is a graphical illustration of the exemplary method of FIG. 2A wherein the rotational speed of the mixing drum is increased to a higher constant rotational speed (S2), and the energy required to rotate the mixing drum containing the fresh concrete mix is measured for a second continuous period of time (as designated at $E_{R2}$), and then the thixotropic built-up structure of the mix is destroyed, as indicated by a leveling off of energy ($E_{R3}$) which is calculated over a subsequent continuous time period.

As shown in FIG. 2, the method involves rotating a mixing drum at various speeds for periods of time to mix completely the concrete mix components or otherwise to maintain the concrete mix in a completely mixed state, as evidenced by little or no fluctuation of $E_R$ over time. Preferably, the speed increases and decreases are done in step-wise fashion, as illustrated in the graph of FIG. 2. As shown in FIGS. 3A-3B, the energy ($E_R$) required to rotate the mixing drum is monitored at these various speed changes.

With reference to FIGS. 2 and 3A-3B, therefore, the present inventors describe another exemplary method of the invention wherein energy measurements are taken after increasing and also after decreasing speed of the mixing drum. This variation ("trapezoid") comprises rotating a mixing drum containing a (completely mixed) concrete mix at a first constant speed ($S_1$) for a specified time period, and measuring the energy required to rotate ($E_R$) the drum at the constant speed. The speed is elevated, preferably by at least one half rotation per minute (rpm) and more preferably by at least one full rpm; and $E_R$ is again measured for a specified time period (FIG. 3A). Preferably, this is done incrementally in one or more steps so that an $E_R$ value for a specified time period is determined ($E_{R2}$, FIG. 3B) once the setting is turned to the highest speed ($S_2$), and then for a specified time period once the energy required to rotate the mixing drum has leveled off for a period of time ($E_{R3}$ in FIG. 3B) at $S_2$. The speed is changed (preferably decreased rather than increased) in stepwise fashion to $S_3$ (which is different from $S_2$ but is most preferably the same as $S_1$), and the energy required to rotate the drum is also measured once the energy required to rotate the mixing drum has leveled off for a period of time ($E_{R4}$, FIG. 3C) at the decreased speed ($S_3$).

Figure 4:
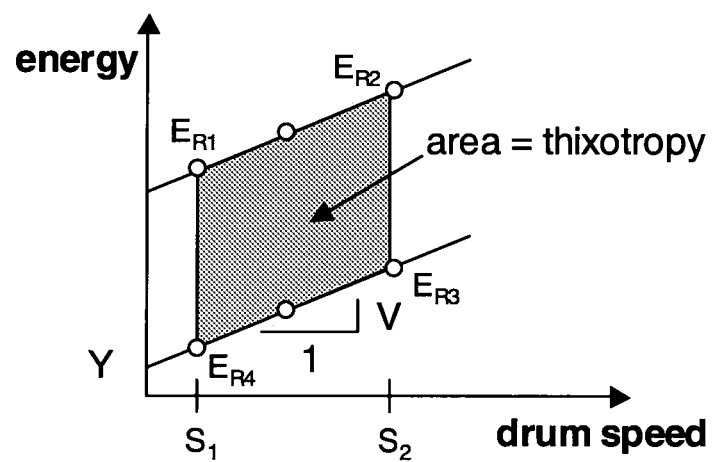
FIG. 4 is a graphical illustration of the exemplary method of FIGS. 2A-2C wherein the energy values $E_{R1}$, $E_{R2}$, $E_{R3}$, and $E_{R4}$ for rotating the mixing containing the concrete mix are plotted against drum rotation speed (shear rate), thereby revealing a trapezoid whose area provides an indication of the thixotropy characteristic of the concrete mix.

Optionally, one or more speed increments can be used between $S_1$ and $S_2$ as illustrated in FIG. 2 in order to generate more energy/speed data points between $E_R$ and $E_{R2}$ as illustrated in FIG. 4. It may be desirable to do this to obtain a more accurate first stress curve.

As indicated in FIG. 3B, the energy required to turn the mixing drum is monitored upon increasing rotational speed to $S_2$, and is measured during another specified time period once the concrete mix has reached a minimum resistance-to-flow for the given mixing speed due to the breakdown of the thixotropic internal structure, as indicated by the relatively flat portion designated at $E_{R3}$. The average energy required to rotate the drum during this third time period is plotted as a point ($E_{R3}$) on the energy vs. drum speed chart of FIG. 4.

Figure 3C:
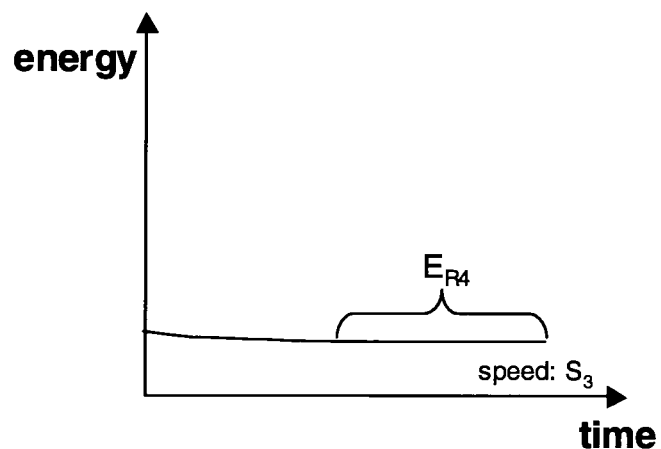
FIG. 3C is a graphical illustration of the exemplary method of FIG. 2B wherein the rotational speed ($S_3$) is decreased (from level $S_2$ to $S_1$) and the energy required to rotate the mixing drum ($E_R$) is monitored until it begins to level off over time (again indicating the mix has reached a minimum resistance to flow for the given mixing speed) and then measured ($E_{R4}$) over another continuous period of time.

As indicated in FIG. 3C, the rotation speed of the drum is changed and preferably this is done by decreasing the speed from $S_2$ to $S_3$. The energy required to turn the drum at $S_3$ is monitored for another specified time period once speed is decreased from $S_2$ to $S_3$, and then for another specified time period after the concrete mix has reached a constant resistance to flow for the given mixing speed due to the breakdown of the thixotropic build-up structure, as indicated by the relatively flat portion designated at $E_{R4}$. The average energy required to rotate the drum during this fourth time period is plotted ($E_{R4}$) on the energy vs. drum speed chart of FIG. 4.

As illustrated in FIG. 4, the four points $E_{R1}$, $E_{R2}$, $E_{R3}$, and $E_{R4}$ illustrate a four-sided shape roughly approximating a trapezoid. This trapezoid defines an area that corresponds to thixotropy of the concrete mix in the delivery truck mixing drum. The concrete mix can therefore be monitored and controlled, using conventional slump control equipment available on ready-mix delivery trucks, by determining the thixotropy value of the concrete in the drum and comparing this to a predetermined thixotropy range of values stored in computer memory, and then adjusting the rheology of the concrete mix accordingly, by addition of liquid additive (water, chemical admixtures) so that the determined thixotropy value conforms with the desired predetermined thixotropy ranges stored in computer memory.

An exemplary method of the invention for monitoring concrete rheology in the delivery truck mixer drum, thus comprises: (A) mixing within a rotating drum of a delivery truck a concrete mix to the point of the concrete mix being completely mixed; (B) rotating the concrete mix at a first constant drum speed ($S_1$) and at least one higher speed ($S_2$) for specified time periods to determine the energy needed for rotating the concrete mix ($E_R$) at each speed; (C) storing the determined first energy value ($E_{R1}$) and second energy value ($E_{R2}$) in computer memory; (D) rotating the concrete mix at $S_2$ to determine a third energy value ($E_{R3}$) for a specified time period, but determining the third energy value ($E_{R3}$) only after $E_R$ has leveled off thereby indicating that the concrete mix has reached a minimum resistance to flow for the given mixing speed due to the breakdown of the thixotropic build-up structure, and storing $E_{R3}$ in computer memory; (E) rotating the concrete mix at a speed ($S_3$) different from (and preferably lower than) $S_2$ to determine a fourth energy value ($E_{R4}$) for a specified time period, but determining the fourth energy value ($E_{R4}$) only after $E_R$ has leveled off (indicating that some fluidity has returned to the mix), and storing $E_{R4}$ in computer memory; (F) comparing at least two on-board yield stress, plastic viscosity, and thixotropy values based on the determined $E_{RS}$, $E_{R2}$, $E_{R3}$, and $E_{R4}$ values with corresponding at least two predetermined ranges of yield stress, plastic viscosity, and thixotropy values stored in computer memory; and (G) adjusting rheology of the concrete mix using a liquid component dispensed onboard the truck to achieve rheology corresponding to at least two predetermined ranges of yield stress, plastic viscosity and/or thixotropy values.

In further exemplary methods of the invention, steps (B) through (G) can be repeated, and the on-board yield stress, plastic viscosity, and/or thixotropy values based on said determined $E_{R1}$, $E_{R2}$, $E_{R3}$, and $E_{R4}$ values in step (F) can be compared to predetermined yield stress, plastic viscosity, and/or thixotropy values corresponding to each of a transit rheology profile or placement rheology profile, as may be desired.

In other exemplary methods, at least one further $E_R$ value is determined for specified time period at a speed greater than $S_1$ but less than $S_2$, and, similarly, for the part of the method in which speed is decreased from $S_2$ to $S_3$, additional step-decreases in rotational speed can be used and additional rotational energy values ($E_R$) can be determined for specified time periods once $E_R$ has leveled off thereby indicating that the concrete mix has reached a minimum resistance to flow for the given mixing speed due to the breakdown of the thixotropic build-up structure.

It may be noted here, with reference to FIG. 4, that the slope of the stress curve between $E_{R4}$ and $E_{R3}$ may be used to calculate a value for plastic viscosity (designated as "V") while the intercept of the slope with the vertical axis designating the "energy" value provides a value for the yield stress (designated at "Y") of the concrete mix in the drum. It is believed that determination of the plastic viscosity and yield stress are more accurately monitored by using data derived from the portion of the aforementioned "trapezoid" method in which energy is measured after a duration at constant speed or after a decrease in speed, since the energy-versus-time measurements will not be affected by a bump in energy required after speed increases (See e.g., $E_{R-MAX}$ in FIG. 1). It is also possible to calculate an estimate of slump flow from measurements of the values for yield stress and plastic viscosity.

In any event, an exemplary method of the invention comprises determining values for plastic viscosity, for yield stress, or both, as well as determining a value for thixotropy of the concrete mix; comparing the determined thixotropy value and at least one of the plastic viscosity value, yield stress value, or both, with predetermined values stored in computer memory. As will be explained further hereinafter, the rheology of the concrete mix can be adjusted, based on the comparison of derived rheology values with predetermined (target) rheology values, by adding a liquid component into the mixing drum.

For the "trapezoid" variation of the method as described above, the rotational speed of the mixing drum can be varied from one half rotation per minute (rpm) to eight or more rpm. Again, increases or decreases of rotational speed should preferably be on the order of at least half (0.5) rpm and preferably by at least one (1) rpm or more. The increase of drum speeds from $S_1$ to $S_2$, which represents the highest speed, as well as the decrease in drum speeds from $S_2$ to $S_3$ (which is preferably the same as $S_1$), should preferably be done in step-wise fashion during successive, intervening continuous time periods. Preferably, the length of continuous time periods represented by $T_1$, $T_2$, $T_3$, and $T_4$, as well as any optional successive, intervening time periods between $T_1$ and $T_2$ and between $T_3$ and $T_4$ should be similar each time the methodology is conducted. The time periods (T) could be as short as 30 seconds and as long as 1-3 minutes or more.

If the initial constant speed $S_1$ is set at one rpm, for example, the mixing drum rotation speed can be incrementally increased by one rpm increments for successive continuous periods, and $E_R$ is determined for each step increase until the highest speed $S_2$ is reached (e.g., 8-12 rpm). After the thixotropy breakdown period elapses and energy ($E_{R3}$) measured at $S_2$ during $T_3$, the rotational mixing speed can be decreased by one rpm in similar stepwise fashion in reverse until it reaches $S_3$ (which is preferably the same as $S_1$).

In discussing the principles embodied in the method of the present invention, the present inventors believe it helpful to define once more some of the concepts pertaining to concrete properties. The term "workability" is sometimes used interchangeably with the concept of "slump" but is more properly descriptive of "that property of freshly mixed concrete or mortar that determines the ease with which it can be mixed, placed, consolidated, and finished to a homogenous condition" (ACI 116R). The term "rheology" is, on the other hand, the scientific description of the flow properties of fluids. While workability can be described in terms of numerous variables, including slump, flowability, compactability, and segregation resistance, rheology is typically described in terms of yield stress, plastic viscosity, and thixotropy. "Yield stress" is the amount of stress or energy needed to initiate or maintain flow in the material, while "plastic viscosity" is the increase in stress per increase in shear rate after the yield stress is exceeded. Thixotropy is the reversible, time-dependent decrease in the viscosity of a fluid subjected to shearing. Terms approximating these parameters, such as the intercept (yield stress) and slope (plastic viscosity) of a line reflecting the relationship between mixer torque and drum rotation speed can also be used. Instead of mixer torque, terms correlated to mixer torque such as hydraulic pressure or amperage can be used.

Due to thixotropy, the shear history of the concrete prior to measurement of yield stress and plastic viscosity should be taken into account. In addition, the amount of thixotropy should be suitable for the application.

Concrete should have correct rheology at the time of placement and correct hardened properties with minimum cost. Often, when concrete is batched at a plant, it does not exhibit the expected rheology. Furthermore, the rheology is likely to change during the time the truck is in transit from the batch plant to the jobsite. As a result, concrete may be batched at the plant with different rheology than that needed at the jobsite with the expectation that the rheology will change over time. Alternatively, water or additives can be used at the jobsite to adjust rheology. Often, only water can be added at the jobsite due to logistical reasons. The use of some additives and especially water may adversely affect hardened properties. Other additives may positively affect hardened properties.

The selection of the optimal additives or water additions and their additions times is highly complex. Therefore, an optimization system is needed to take into account relevant parameters and determine the optimal initial mix proportions batched at the plant and the type, amount, and addition time of additives used after batching and until discharge of concrete at the jobsite.

The rheology monitoring and control system of the present invention selects: initial batch mix proportions, additive type(s), additive and/or water amounts, and addition time(s) of additive(s) and/or water; based on: user-defined target concrete properties, predicted effects of initial mix proportions and additives on rheology, predicted effects of initial mix proportions and additives on hardened properties, and costs; where the predictions of the effects on rheology and hardened properties are based on: current concrete rheology, mixing time, mixing speed, ambient temperature, ambient humidity, concrete temperature, concrete truck characteristics (for example, drum geometry, drum materials, drum condition), concrete load size, concrete raw material characteristics, concrete mix proportions, time until placement (discharge), the time required to convert the concrete mix (such as from transit rheology to placement rheology), pre-programmed relationships between materials and concrete properties, and historical data collected by the system; to ensure optimal rheology at specific times, optimal hardened properties at specific times, and optimal cost.

The rheology of the concrete at times other than placement can be important and are considered by the system. The rheology of the concrete during mixing can affect the efficiency of mixing and the efficacy of additives. The rheology after placement and until setting can affect such properties as horizontal pressure exerted by concrete against formwork and resistance to segregation. To reduce formwork pressure and increase segregation resistance, the concrete should be fluid at the time of placement but become less fluid quickly after the end of placement.

Additives may be used to adjust hardened properties. Additives used to adjust rheology may affect hardened properties. The system can select the optimal type, amount, and addition time to ensure correct hardened properties.

The system can also adjust the initial proportions of materials loaded into the mixer at the batch plant as part of the method of optimizing the concrete rheology, hardened properties, and cost. Due to the limited space on a truck, a greater number of materials will likely be available at the plant. Adjustments to initial batch proportions can be based on feedback data from other batches, expected conditions subsequent to the time of batching, and other pre-established relationships.

Thus, a conceptual framework for monitoring and adjusting concrete during a delivery operation which is conceived in terms of a transit portion and placement portion, involves the following determinations in the thixotropy determining step (step B): at least one value corresponding to the thixotropy of the concrete mix during transit from a mix plant or dispatch center to the placement site is determined and this determined value is compared to a predetermined value desired for the concrete during the transit portion of the delivery of the concrete; at least one adjustment is made to the concrete mix by adding a liquid component thereto, based on the comparison of the determined transit thixotropy with the predetermined value desired for the concrete during the transit portion of the delivery; at least one value corresponding to the thixotropy of the concrete mix at placement is determined and this determined value is compared to a predetermined value for the concrete at placement; and at least one adjustment is made to the concrete mix by adding a liquid component thereto based on the comparison of the determined placement thixotropy to the predetermined value desired for the concrete at placement. In further embodiments, the determination as to when to adjust the concrete mix based on the comparison of the determined placement thixotropy to the predetermined value desired for the concrete at placement can be based on at least one of factors that are predetermined and selected from the following: concrete mix components, volume of concrete mix, the effect of liquid additions to the concrete mix, estimated transit time from batching plant or dispatch center to placement, estimated waiting time at placement site, traffic congestion, ambient temperature, concrete temperature, humidity, minimum time needed to mix separate components into uniform mix, minimum time needed to incorporate and to mix completely a liquid component introduced into the concrete, minimum time needed to convert the concrete mix from transit rheology to placement rheology, and topography. As mentioned above, this methodology is particularly suited for delivery of highly fluid concrete, such as SCC.

Figure 6:
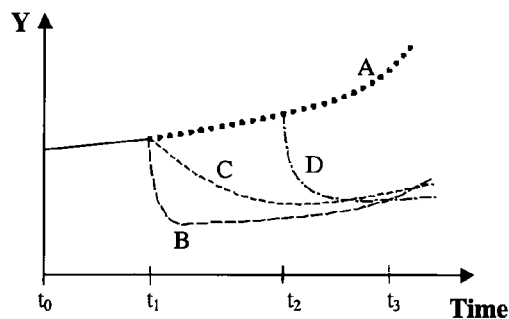
FIGS. 6-7 are graphs illustrating multiple predictions of rheology over time based on the use of different additives at different times.
Figure 7:
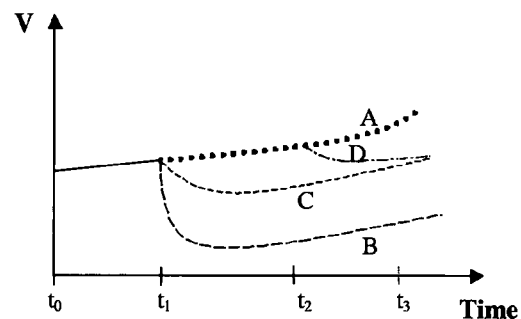

The effect of the methods of the present invention can be illustrated with reference to FIGS. 5-7. The box depicted in FIG. 5, for example, represents the optimal range of rheological parameters Y and V at the time of placement (moment of discharge) for the intended concrete mix application. FIGS. 3 and 4 show multiple predictions of rheology over time with regard to rheology parameters Y and V, respectively, based on the use of different additives at different times. If no modifications are made to the concrete, the concrete will have unsuitable rheology at the time of placement (as designated by the intercept of the line at "A" with $t_3$). Case "B" indicates the addition of an additive at time $t_1$. The rheological properties at the time of placement are unsuitable at the time of placement for rheology parameter V (as shown in FIG. 7). Cases "C" and "D" indicate the effects of two different additives added at different times, but both provide the correct rheology at the time of placement (at $t_3$ in FIGS. 6 and 7). Therefore, Case C or Case D would be selected based on their costs or effects on hardened properties. The system will continuously monitor the conditions and make adjustments accordingly.

The rheological parameters used by the system (e.g. Y and V in FIG. 5) may be those specified by the user. The user may specify parameters such as slump flow or yield stress, and the system can determine the corresponding values of Y, V, and other parameters. Hence, the desired rheological parameters desired (hereinafter "workability box") can be refined over time as data from field placements is collected (e.g., FIG. 5).

Figure 8:
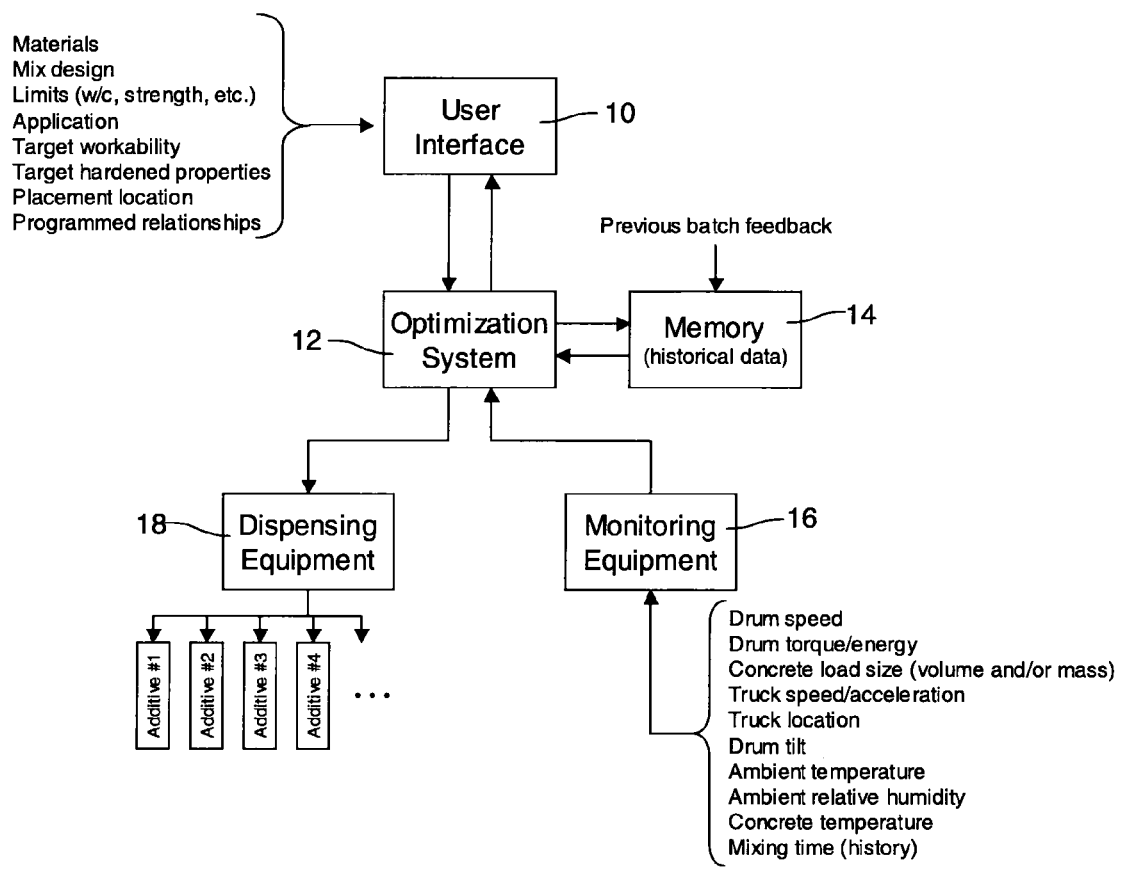
FIG. 8 is a flow chart showing an exemplary system for monitoring and controlling concrete rheology in a concrete delivery in which the method of the invention can be implemented.
Figure 9:
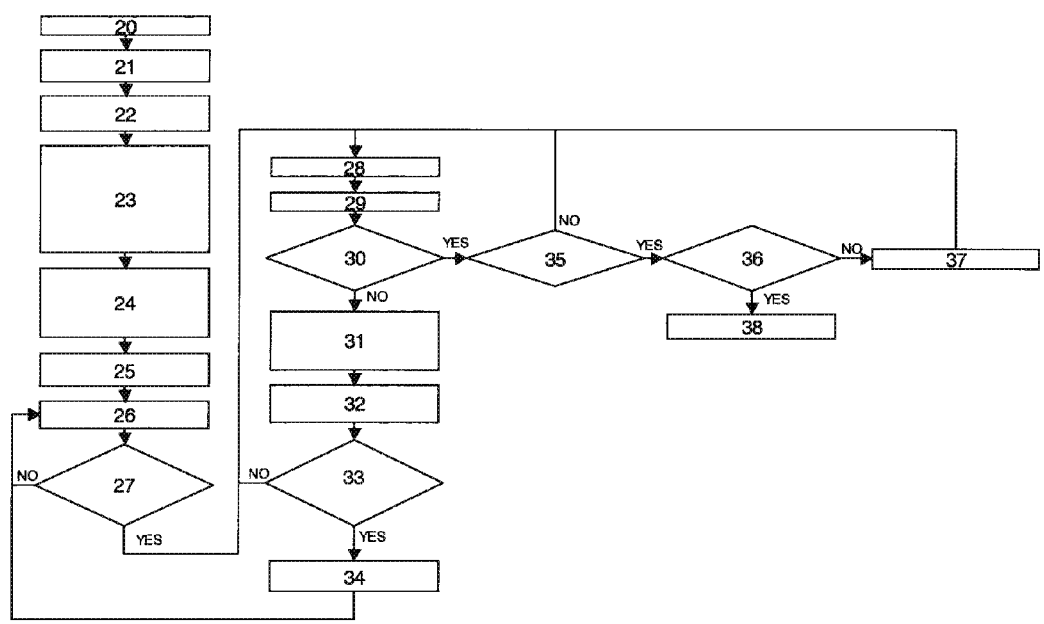
FIG. 9 is a flow chart illustrating a typical concrete mix management and optimization system in which an exemplary method of the invention for monitoring rheology of concrete mixes is employed.

The system for implementing the methods of the invention is diagramed in the flow chart of FIG. 8, while the method for managing and optimizing the concrete mix from the batch plant to the concrete discharge point is shown in FIG. 9. The methods for measuring Y (reflecting yield stress), V (reflecting plastic viscosity, and X (reflecting thixotropy) were previously shown above in FIGS. 2-4.

As shown in FIG. 8, an exemplary rheology monitoring and control equipment system installed on a concrete delivery truck, suitable for enabling methods of the invention to be used, involves a computer processing unit CPU (12) or optimization system that can be connected to computer (accessible) memory 14, sensors for monitoring the equipment on the truck 16, and dispensing equipment for adjusting/controlling 18 slump and rheology of the concrete mix. The user interface 10 can be a keyboard or touch screen monitor conventionally used for inputting data into the optimization system 12 which comprises a CPU having the requisite application software and access to computer memory 14 for storing and retrieving historical data such as predetermined (target) slump and rheology ranges data (e.g., yield stress, plastic viscosity, and/or thixotropy values) as well as for storing slump and rheology data that is determined on-board the concrete delivery truck in real time. The user can input information about the concrete mix materials (components), mix design, specifications or limitations (such as water/cement ratio, strength parameters, etc.), concrete application information, target workability or slump values (e.g., transit rheology profile, placement rheology profile), target hardened properties in the concrete after placement, placement location, and other programmed relationships (such as correlations between the workability and/or rheology of a given concrete mix and its constituent material properties, as will be further discussed hereinafter). This information is stored in computer memory 14, which can also be used for storing information determined from on-board delivery operations on a batch-by-batch basis. The optimization system 12 is electrically connected to monitoring equipment which may include, by way of example, sensors and related equipment for measuring rotational drum speed, the energy (hydraulic or electric) required for rotating the concrete mixing drum on the truck, load size of the concrete mix (whether by volume or mass), truck speed, truck acceleration, truck location, tilt angle of the mixing drum, ambient temperature, ambient humidity, concrete temperature, and mixing time. The optimization system 12 is also electrically connected to dispensing equipment for metering any number of additives, preferably in liquid form, into the concrete mixing drum. The additives could include water, a water-reducer (such as high range water-reducers or so-called superplasticizers), a viscosity-modifying agent, and other additives (18).

FIG. 9 is a flow chart of an exemplary method involving the use of conventional concrete delivery truck equipment wherein the method of the present invention can be employed to monitor and control rheology of the on-board concrete mix. The steps are summarized as follows.

The user inputs various information pertaining to the concrete mix, such as the component materials and mix design (designated as at 20).

The desired or target workability (e.g. slump or slump flow) and/or rheology values (yield stress, plastic viscosity, and/or thixotropy) are inputted or determined (designated as at 21). These inputs may altogether be referred to as the "workability box" parameters and may include a particular set of slump and rheology criteria pertaining to separate portions of the delivery operation, such as the "transit rheology profile," relative to the properties of the concrete mix after leaving the ready-mix plant or dispatch center, and the "placement rheology profile," which pertains to the condition of the concrete at the time of discharge at the construction site where the concrete is to be placed.

The user may enter information pertaining to the estimated batch time and discharge time (designated as at 22). Alternatively, this information can be pre-programmed into the system or derived by the system based on historical batch data. Also, the batch time information would be different if the truck is loaded with a pre-mixed concrete mix, or if the components (e.g., water, cement, sand, admixture or admixtures, fibers) were introduced such that the delivery truck mixing drum would need to be rotated in order to mix the components together. Entering the scheduled discharge time would allow the system to determine whether there was sufficient time for the concrete mix to be prepared (such as by introducing liquid additives (e.g., superplasticizers, viscosity modifiers, water, etc.) so as to meet the target. The intent behind entering the batch time and discharge time is to calculate how long the concrete will be in the truck, and, hence, to calculate the time needed for monitoring the concrete mix and making adjustments so that the mix conforms, at the appropriate times, to predetermined (target) transit and placement rheology profiles. Depending on the level of automation of the system, batch time may be recorded as it occurs without the need for the operator to enter it into the computer; and, thus, more preferably the actual batch time would be programmed into the system or derived by the system based on historical batch data.

The relationships and correlations between a particular concrete mix design, the effect of particular additions (water, chemical admixtures) on the particular concrete mix and batch proportions may also be inputted (designated as at 23). Preferably, this information would be collected by the system, and the system would be "trained" based on historical data.

Information regarding the predicted effects of multiple initial batch proportions, and types and amounts, and addition times of additives (admixtures) and/or water on the rheology of the concrete over time, along with information regarding the properties of the concrete when hardened can be inputted into the computer memory. More preferably, this information could be derived by the system based on historical batch data, such that the system was in effect being "trained" with each delivery operation.

The user can select optimal initial batch proportions and additives/admixtures and/or water additions (designated as at 24), and this kind of information can also be derived by the system based on historical batch data, such that the system was in effect being "trained" with each delivery operation.

The concrete delivery truck mixer drum is then loaded with initial batch proportions (designated as at 25), the concrete mix or mix components are then rotated in the mixer drum while the energy to rotate the drum (or mixer torque) is measured (designated as at 26), and the system assesses whether mixing is completed by (designated as at 27). As previously mentioned, this is accomplished by measuring the torque at constant drum rotational speed until the fluctuation of torque over time reaches a predetermined value or range, and then rheology factors can be assessed, such as thixotropy (e.g., implementing the "torque fade" or trapezoid methods as previously discussed) as well as plastic viscosity, yield stress, slump, and/or slump flow (28).

The discharge time can be estimated or inputted (designated as at 29) based on the same process as discussed for 22 above.

After the rheology measurement 28 is accomplished and a set of on-board rheology values are determined (at least two values selected from yield stress, plastic viscosity, and thixotropy), these are compared to the predetermined yield stress, plastic viscosity, and thixotropy values stored in computer memory, which values are otherwise referred to as the "workability box" values that have been programmed or selected for that point in time during the delivery operation (designated as at 30). If the determined on-board rheology values do not fall within the workability box, then the system reviews the predicted effects of additives (e.g., admixtures) and/or water which have been stored in computer memory in accordance with additive type, amount, and additional times required (designated as at 31). The system then selects the optimal additives and/or water addition (designated as at 32). The system then may consider the current time in the delivery operation and the time for dispensing the additive(s) (designated as at 33), and a signal is sent by the system CPU to the appropriate dispensing device for dispensing the appropriate kind and amount of additive at the appropriate time (designated as at 34); and the system then recycles back through steps 26 mix the additive into the concrete mix and measure its torque (26), measure mix rheology (28) until the target rheology parameters (workability box at 30) are met.

In further exemplary methods of the invention, the system can ensure that all additives are properly incorporated into the concrete mix (designated as at 35) at the appropriate time so that the placement rheology profile is met at the currently scheduled discharge time (designated as at 36). If the placement rheology profile is met, the concrete mix is discharged (designated as at 38) or, if there is a pause or delay in delivery, the system can continue to monitor and make adjustments (37) and recycle through the monitoring, comparison, mixing, and adjustment steps as necessary.

Thus, the present inventors believe that the present invention permits concrete to be delivered to a jobsite with optimal rheology at specific times during transit and during placement, and also with optimal hardened properties at specific times, and can accomplish this in an optimal manner in terms of cost and performance. The method can be used in conventional slump monitoring equipment to ensure optimal rheology at the most critical times, such as at the time of placement. The system also permits workability data to be stored over time, so that the workability box (or target rheology profile for transit as well as for placement) can be refined over time based on feedback from previously batch deliveries. The system can accomplish these benefits while minimizing the necessity for human involvement.

In further exemplary methods of the invention, wherein the on-board rheology of the concrete mix is compared to a predetermined target transit rheology profile and a predetermined placement rheology profile, and wherein both rheology profiles involve monitoring at least two of the factors selected from yield stress (Y), plastic viscosity (V), and thixotropy (X), the transition in monitoring mode from transit rheology profile to placement rheology profile may be accomplished by having the system consider one or more of the following factors: such as concrete mix components, volume of concrete mix, the effect of liquid additions to the concrete mix (e.g., water, chemical admixtures), estimated transit time (from batching plant or dispatch center to placement site), estimated waiting time at the placement site, traffic congestion (during transit and/or at placement site), ambient temperature and/or concrete temperature (during transit and/ or at placement site), humidity levels, minimum time needed to mix separate components into uniform mix (if components separately loaded at batch site and the concrete is to be mixed during transit), minimum time needed to incorporate and to mix completely a liquid component introduced into the concrete, minimum time needed to convert the concrete mix from transit rheology to placement rheology, topography (e.g., whether terrain and roads are flat, bumpy, inclined, straight, or curved), and other factors (e.g., such as may be derived from global positioning systems (GPS) such as estimated time of arrival, traffic congestion).

Figure 10:
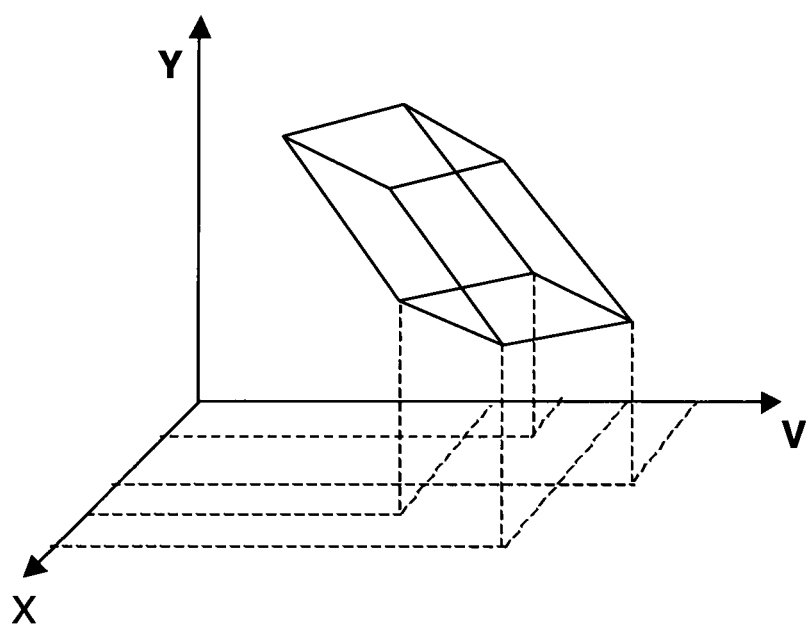
FIG. 10 is a graphic illustration of a "workability box" or predetermined (target) rheology profile.

As shown in FIG. 10, the methods of the invention for measuring Y (reflecting yield stress), V (reflecting plastic viscosity), and X (reflecting thixotropy), as previously discussed above and shown in FIGS. 2-4, can be visualized in terms of a three-dimensional rheological profile or "workability box." Thus, in further exemplary embodiments of the invention, the yield stress (Y), plastic viscosity (V), and thixotropy (X) can be monitored on-board the concrete delivery truck during the transit phase and/or placement phase of the delivery operation and displayed on a computer monitor or printed out.

The on-line measurements for Y, V, and X can also visually be compared with a predetermined rheological profile or "workability box" (depicted as a three-dimensional shape defined as ranges along each of the X, V, and Y axes in FIG. 10) to provide the user or customer with a visual display or representation of on-board rheology in comparison with the predetermined or target rheology profile. For example, a point or cluster of points (not shown) corresponding to the on-board determined values V, Y, and/or X for the concrete mix can be visually represented with respect to the "workability box" so as to provide the user, truck driver, customer, or concrete ready-mix supplier a visual indication as to whether the rheology of the concrete mix is within the predetermined (target) ranges stored in the computer memory.

Figure 5:
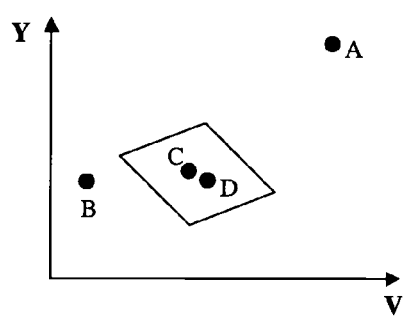
FIG. 5 is a graph representing an optimal range of rheological parameters, wherein correct rheology at placement (designated at C and D within a "workability box" surrounding C and D) can be provided by using the method of the present invention wherein additives are dosed at the proper amount and at the proper times, whereas improper rheology at placement (designated at A and B) can obtained with no additive (e.g., A) or with additive (e.g., B) if the improper amounts and/or times are used.

With regard to FIGS. 5 (two-dimensional) and FIG. 10 (three-dimensional), further exemplary methods of the invention comprise illustrating at least two of predetermined transit or placement rheology values selected from yield stress (Y), plastic viscosity (V), and thixotropy (X) and illustrating these values, on a monitor, paper, or other visual display, as a two- or three-dimensional box, and monitoring at least two rheology values of the concrete mix corresponding to yield stress (Y), plastic viscosity (V), and/or thixotropy (X) and illustrating these values as dots, points, or other objects in relative spatial relation with the illustrated two- or three-dimensional box.

Further examplary methods of the invention provide for measurement of plastic viscosity (V), yield stress (Y), and thixotropy (X) values of concrete in the mixing drum, comparing these values to at least one set of predetermined (target) values stored in computer memory, and making adjustments to the concrete mix to conform its rheology to the stored values by introducing a predetermined amount of liquid component operative to adjust the mix to the predetermined rheology. More preferably, the V, Y, and X values are compared to at least two sets of predetermined (target) values, such as one set which corresponds to a transit rheology profile, and another set which corresponds to a placement rheology profile.

An exemplary method of the invention is suitable for delivery SCC. The SCC is adjusted during a transit phase to a rheology value corresponding to a slump of 0 to 11 inches in the mixing drum during a delivery operation; and is subsequently adjusted during the placement phase of the delivery operation to a high slump flow greater than 18 inches, based on values determined during step B; and the thixotropy of the concrete is measured during the placement phase, and optionally also during the transit phase.

While the invention is described herein using a limited number of embodiments, these specific embodiments are not intended to limit the scope of the invention as otherwise described and claimed herein. Modification and variations from the described embodiments exist. More specifically, the following example is given as a specific illustration of an embodiment of the claimed invention. It should be understood, that the invention is not limited to the specific details set forth in the example. All parts and percentages in the examples, as well as in the remainder of the specification, are by volume unless otherwise specified.

Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited. For example, whenever a numerical range with a lower limit, RL, and an upper limit RU, is disclosed, any number R falling within the range is specifically disclosed. In particular, the following numbers R within the range are specifically disclosed: R=RL+k*(RU−RL), where k is a variable ranging from 1% to 100% with a 1% increment, e.g., k is 1%, 2%, 3%, 4%, 5%. . . . 50%, 51%, 52%, . . . 95%, 96%, 97%, 98%, 99%, or 100%. Moreover, any numerical range represented by any two values of R, as calculated above, is also specifically disclosed.

EXAMPLE 1

If one were to employ the slump monitoring ready-mix trucks commercially available from RMC Industries Corporation of Georgia and RS Solutions, Inc. of Ohio, one could monitor and control slump and rheology of concrete mixes as shown in Table 1. In the present example, the system can monitor slump initially during the transit portion of the delivery operation and control the rheology of the concrete so that it conforms to a predetermined "target transit rheology", and at some point, the system can decide to switch by making adjustments to the concrete rheology in accordance with a "target placement rheology."

To begin, the user programs into the system the requirements for the concrete mix design, which in this present example calls for a self-consolidating concrete (SCC) having a 24-26 inch slump flow and other properties. When the concrete mixing truck enters the batch plant, the system can request, or otherwise determines by input from the user, information such as time of placement, a rheology profile of the concrete mix during transit from the plant to the placement site (otherwise referred to as the "target transit rheology"), a rheology profile of the concrete mix which is desired at the placement site (otherwise referred to as the "target placement rheology"), the time needed for changing from the target transit rheology to the target placement rheology, and initial batch portions needed for achieving transit rheology initially.

The target placement rheology may be minimal, requiring monitoring of slump only, using the conventional slump monitoring system.

However, the present invention permits monitoring of slump flow as well as slump, but allowing for the user to enter into the system information regarding the slump flow and workability parameters for the factors yield stress (Y), plastic viscosity (V), and thixotropy (X). This is preferably done as two or more data sets corresponding to at least one target transit rheology data set and at least one target transit rheology data set.

After the concrete delivery truck is loaded with fresh concrete, or with the components for making the fresh concrete, the mixing drum is rotated at an initial mixing speed to mix the component completely together. The system then can begin measurement of the slump estimate for determining whether the target transit rheology is achieved. If this initial target transit rheology is not achieved, the system may, for example, make adjustments such as by dispensing 20 gallons of water and 10 ounces (oz) of high range water reducer (HRWR) into the drum and starts mixing.

When mixing is complete, the system again starts continuous measurement of the slump of the concrete mix, and confirms that the target transit rheology is achieved.

When the truck departs from the plant, the system re-estimates the time to change from the transit rheology to placement rheology, and the time of placement. During transit, the system can detect when the on-board rheology falls below the target transit rheology profile and determines an optimal adjustment, such as by incorporating 12 oz of high range water reducer (HRWR), and starts mixing.

When mixing is complete, the system can restart the continuous measurement of rheology (in this case slump) and make any adjustments until the target transit rheology is achieved.

If the mixing truck is delayed, such as due to delays during transit or at the placement site, the system can re-estimate a new time to change from transit to placement rheology and a new placement (discharge) time.

When the time comes for the system to change from monitoring the concrete mix for transit rheology to placement rheology, the system then determines the optimal adjustment to be made (e.g., delivery of 200 oz high range water reducer (HRWR) and 10 oz of viscosity modifying agent or admixture ("VMA")) and starts mixing.

Once mixing is complete, the system, now monitoring the concrete mix to determine whether the on-board rheology conforms the target placement rheology, initiates the "trapezoid" methodology. The system then monitors yield stress (Y), plastic viscosity (V), and/or thixotropy (X), and preferably all three of these rheology factors, and compares them to predetermined target placement rheology profiles stored in computer memory. This target profile can be referred to as a "workability box" which, as illustrated in FIG. 10, can be envisioned as a three-dimensional graph in which the on-board values for Y, V, and X can be compared with predetermined (target) ranges shown as the workability box illustrated in FIG. 10. If Y, V, or X are outside the target placement profile (workability box), the system then determines an optimal adjustment (e.g., 25 oz HRWR and 15 oz VMA), causes the dispensers to inject the necessary liquid components into the concrete mix to make the adjustment, and begins mixing the concrete.

After mixing is completed, the system can again monitor the rheology state of the concrete mix using the trapezoid methodology. This process is repeated until the point in time desired for placement of the concrete, when the driver begins actual discharge of the concrete mix at the placement site.

The example of the method as narrated above is summarized in table 1 below.

TABLE 1

| Event Time | Slump | Slump Flow | Y | V | X | Action |
|---|---|---|---|---|---|---|
| 10:00 | | | | | | User requests concrete mix ID 4205, which is SCC with 24 to 26-inch slump flow, 5,000 psi compressive strength, and maximum water-to-cement ratio of 0.40. User inputs address of placement. |
| 10:01 | | | | | | Truck enters batch plant, ready for loading. System determines estimated time of placement (11:00), target transit rheology (5 in. slump), target placement rheology (24 to 26-in. slump flow and workability box in terms of Y, V, X), time to change from transit to placement rheology (10:45), and initial batch proportions to achieve transit rheology. |
| 10:02 | | | | | | Concrete truck is loaded. Mixing begins. |
| 10:06 | | | | | | Mixing complete. System starts measurement of slump estimate. |
| 10:07 | 2 in. | | | | | Transit rheology not achieved. System determines optimal adjustments as 20 gal of water and 10 oz of HRWR, dispenses water and HRWR into mixer, and starts mixing. |
| 10:10 | | | | | | Mixing complete. System starts continuous measurement of slump estimate. |
| 10:11 | 5 in. | | | | | Transit rheology achieved. |
| 10:12 | 5 in. | | | | | Depart plant. System re-estimates time to change from transit to placement rheology (10:47) and time of placement (11:02). |
| 10:24 | 4 in. | | | | | Transit rheology below target. System determines optimal adjustment as 12 oz of HRWR, dispenses HRWR, and starts mixing. |
| 10:26 | | | | | | Mixing complete. System restarts continuous measurement of slump estimate. |
| 10:27 | 5 in. | | | | | Transit rheology achieved. |
| 10:35 | 5 in. | | | | | Mixing truck delayed. System estimates new time to change from transit to placement rheology (10:50) and new discharge time (11:05). |

TABLE 1-continued

| Event Time | Slump | Slump Flow | Y | V | X | Action |
|---|---|---|---|---|---|---|
| 10:50 | 5 in. | | | | | Time to adjust from transit to placement rheology. System determines optimal adjustment as 200 oz. HRWR and 10 oz. VMA. System dispenses additives and starts mixing. |
| 10:54 | | | | | | Mixing complete. System starts trapezoid methodology. |
| 10:55 | | 23 in. | 0.42 | 0.81 | 0.42 | Trapezoid methodology complete. Slump flow target not achieved and Y, V, X not in target workability box. System determines optimal adjustments as 25 oz HRWR and 15 oz VMA, dispenses HRWR and VMA, and starts mixing. |
| 10:58 | | | | | | Mixing complete. System starts trapezoid methodology. |
| 10:59 | | 26 in. | 0.21 | 0.73 | 0.40 | Trapezoid methodology complete. Slump flow target achieved and Y, V, X in workability box. System continues trapezoid methodology. |
| 11:05 | | 26 in. | 0.21 | 0.75 | 0.42 | Placement time. Slump flow on target and X, Y, Z in workability box. Driver begins concrete discharge. |
| 11:13 | | | | | | Discharge complete, driver returns truck to plant. |

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Skilled artisans can make variations and changes without departing from the spirit of the invention.

the invention claimed is:

1. A method for monitoring thixotropy of concrete, comprising:
    (A) rotating a concrete mix, or the components of a concrete, in a concrete mixing drum at a first mixing speed ($S_1$) to mix completely the concrete mix components or otherwise to maintain the concrete in a completely mixed state; and
    (B) measuring the thixotropy of the concrete mix by monitoring the reversible, time dependent change in viscosity occurring after rotational speed of the concrete mix in the mixing drum is altered by changing to another speed ($S_2$) that is different from $S_1$, said concrete mix thixotropy measuring being accomplished by
       increasing the speed of the mixing drum to a faster constant mixing speed $S_2$ such that $S_2$ is at least one half revolution per minute faster than $S_1$;
       monitoring the energy required to rotate the mixing drum ($E_R$) at constant speed $S_2$ $_{until\ after\ ER}$ levels off over time; and
       storing in computer memory a first value corresponding to the maximum energy required to rotate the mixing drum ($E_{R-MAX}$). after increasing the mixing speed from $S_1$ to $S_2$ and also storing in computer memory a second value corresponding to the average energy required to rotate the mixing drum during a predetermined time period wherein the energy required to rotate continuously the mixing drum at constant speed $S_2$ begins to level off to a minimum level ($E_{R-MIN}$);
    (C) comparing said $E_{R-MAX}$ and $E_{R-MIN}$ values to at leas one set of predetermined target values stored in computer memory; and
    (D) adjusting yield stress, plastic viscosity, or thixotropy of said concrete mix contained in said rotating mixing drum using a liquid component, based on comparing said $E_{R-MAX}$ and $E_{R-MIN}$ values to at least one set of predetermined target values stored in computer memory.

2. The method of claim 1 wherein a value determined by taking the difference between or ratio of $E_{R-MAX}$ and $E_{R-MIN}$ values is compared to a predetermined or target value stored in computer memory.

3. The method of claim 1 wherein step B comprises
    determining the first energy value ($E_{R1}$) required for rotating said concrete mix at $S_1$ and rotating the mixing drum at least one higher speed ($S_2$) greater than $S_1$ for a specified time period to determine the energy needed for rotating the concrete mix ($E_{R2}$) at the at least one higher speed ($S_2$)
    storing said determined first energy value ($E_{R1}$) and determined second energy ($E_{R2}$) values in computer memory;
    rotating said concrete mix at $S_2$ to determine a third energy value ($E_{R3}$) for a specified time period, but determining the third energy value ($E_{R3}$) only after the energy required to rotate the drum has leveled off at. $S_2$, and storing $E_{R3}$ in computer memory;
    rotating said concrete mix at a speed ($S_3$) different from $S_2$ to determine a fourth enemy value ($E_{R4}$) for a specified time period, but determining a fourth energy value ($E_{R4}$) only after $E_R$ has leveled off, and storing $E_{R4}$ in computer memory;
    comparing relative rheology values based on said determined $E_{R1}$, $E_{R2}$, $E_{R3}$, and $E_{R4}$ values with predetermined values stored in computer memory; and
    adjusting rheology of said concrete mix using a liquid component.

4. The method of claim 3 wherein $S_3$ is loss than $S_2$.

5. The method of claim 4 wherein $S_3$ is the same as $S_1$.

6. The method of claim 1 further comprising, in step B, determining values for plastic viscosity, for yield stress, or both, as well as determining a value for thixotropy of the concrete mix;
    comparing the determined thixotropy value and at least one of the plastic viscosity value, yield stress value, or both, with predetermined values stored in computer memory; and
    adjusting the theology of the concrete mix by adding a liquid component into the mixing drum.

7. The method of claim 1 wherein, in step B, at least one value corresponding to the thixotropy of the concrete mix during transit from a mix plant or dispatch center to the placement site is determined and this determined value is compared to a predetermined value desired for the concrete during the transit portion of the delivery of the concrete;

at least one adjustment is made to the concrete mix by adding a liquid component thereto, based on the comparison of the determined transit thixotropy to the predetermined value desired for the concrete during the transit portion of the delivery;

at least one value corresponding to the thixotropy of the concrete mix at placement is determined and this determined value is compared to a predetermined value far the concrete at placement; and at least one adjustment is made to the concrete mix by adding a liquid component thereto based on the comparison of the determined placement thixotropy to the predetermined value desired for the concrete at placement.

8. The method of claim 7 comprising determining when to adjust the concrete mix based on the comparison of the determined placement thixotropy to the predetermined value desired for the concrete at placement, said determination being based on et least one of factors selected from nature of the concrete mix components, volume of concrete mix, the effect of liquid additions to the concrete mix, estimated transit time from botching plant or dispatch center to placement, estimated waiting time at placement site, traffic congestion, ambient temperature, concrete temperature, humidity, minimum time needed to mix separate components into uniform mix, minimum time needed to incorporate and to mix completely a liquid component introduced into the concrete, minimum time needed to convert the concrete mix from transit theology to placement rheology, and topography.

9. The method of claim 1 wherein the concrete mix is self-consolidating concrete.

10. The method of claim 9 wherein the self-consolidating concrete is adjusted during a transit phase to a rheology value corresponding to a slump of 0 to 11 inches in the mixing drum of a delivery truck during a delivery operation; and adjusted during a placement phase of said delivery operation to a high slump flow greater than 18 inches, based on value determined during step B.

11. The method of claim 1 wherein step A comprises monitoring continuously the energy required to rotate the mixing dram ($E^R$) over a continuous time period until such time that the fluctuation of $E^R$ is less than a predetermined fluctuation level, and thereafter initiating step B.

12. The method of claim 1 wherein the speed S1 and S2 differ by between 1 and 25 drum rotations per minute.

13. The method of claim 1 wherein a concrete delivery truck is employed having a closed loop speed control system for automatically controlling the rotational speed of the mixing drum.

14. The method of claim 1 wherein the on-board rheology of the concrete mix is compared to a predetermined transit rheology profile and to predetermined placement theology profile, and wherein both rheology profiles involve monitoring at least two of the factors selected from yield stress (Y), plastic viscosity (V), and thixotropy (X); said method further comprising selecting a transition point whereby rheology is compared to the predetermined placement theology profile rather than the predetermined transit rheology profile, said transition point being determined based on apt least one of the following factors selected from concrete mix components, estimated transit time from hatching plant or dispatch center to placement Site, estimated waiting time at the placement site, traffic congestion during transit or at placement site, temperature during transit or at placement site minimum time needed to mix separate components into uniform mix where components are separately loaded at batch site and the concrete is to be mixed during transit, and the minimum time needed to convert the concrete mix from transit rheology to placement theology.

15. The method of claim 14 wherein at least two of predetermined theology values selected from yield stress (Y), plastic viscosity (V), and thixotropy (X) are illustrated on a monitor or other display device as a two- or three-dimensional box, and at least two rheology values determined from the concrete mix corresponding to yield stress (Y), plastic viscosity (V), and/or thixotropy (X) are illustrated as dots or points in relative spatial relation with said illustrated two- or three-dimensional box.

* * * * *